United States Patent [19]
Welker

[11] Patent Number: 5,907,107
[45] Date of Patent: May 25, 1999

[54] HEATED INSTRUMENT REGULATOR TIP

[75] Inventor: Brian H. Welker, Sugar Land, Tex.

[73] Assignee: Welker Engineering Company, Sugar Land, Tex.

[21] Appl. No.: 08/935,640

[22] Filed: Sep. 23, 1997

[51] Int. Cl.[6] ........................................ G01N 1/00
[52] U.S. Cl. ........................................ 73/863.11; 137/341
[58] Field of Search ........................ 73/863.11, 863.83, 73/863.86; 137/341

[56] References Cited

U.S. PATENT DOCUMENTS

| | | | |
|---|---|---|---|
| 3,653,399 | 4/1972 | Steele | 137/341 |
| 4,346,611 | 8/1982 | Welker | 73/863.86 |
| 4,387,592 | 6/1983 | Welker | 73/198 |
| 4,594,904 | 6/1986 | Richter | 73/863.11 |
| 4,631,967 | 12/1986 | Welker | 73/861.25 |
| 5,224,510 | 7/1993 | Pericles | 137/341 |
| 5,520,211 | 5/1996 | Schonstein et al. | 137/341 |

OTHER PUBLICATIONS

GO, Inc. Bulletin 106–5 "HPR–2 Series Heated Adjustable Pressure Regulator", undated, pp. 1–4.

*Primary Examiner*—Robert Raevis
*Attorney, Agent, or Firm*—Herzog, Crebs & McGhee; Bruce E. Burdick

[57] ABSTRACT

A heated instrument regulator tip is shown for use in retrieving samples from the interior of a natural gas or similar pipeline. A well is disposed within the tip and adapted to receive an electrical heater. The heater supplements thermal fins on the tip to transfer thermal energy to the gas sample inside the tip. The thermal energy counteracts the Joule-Thompson cooling of the gas due to the rapid pressure drop, thus preventing freeze up or condensation within the regulator tip.

11 Claims, 2 Drawing Sheets

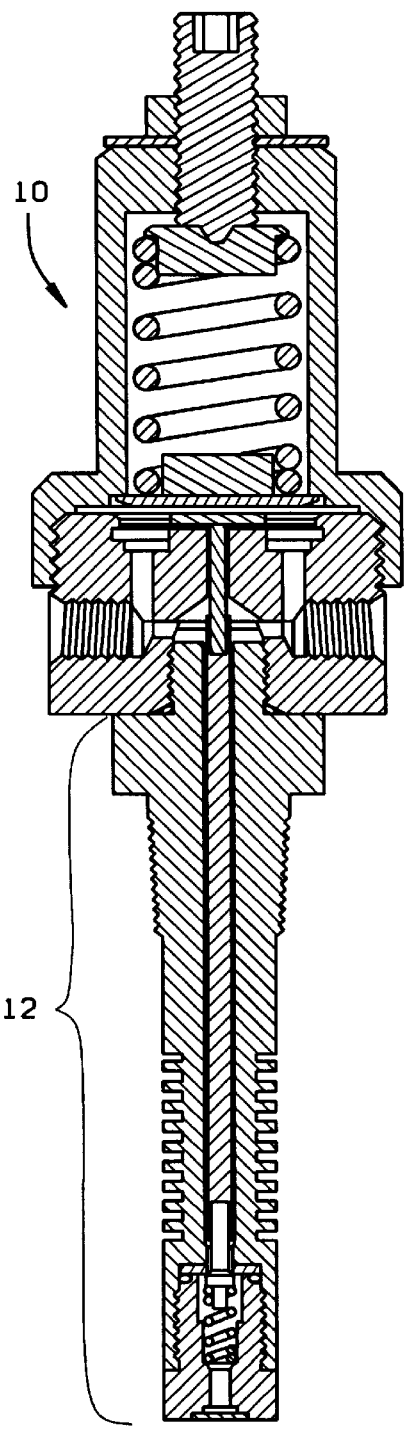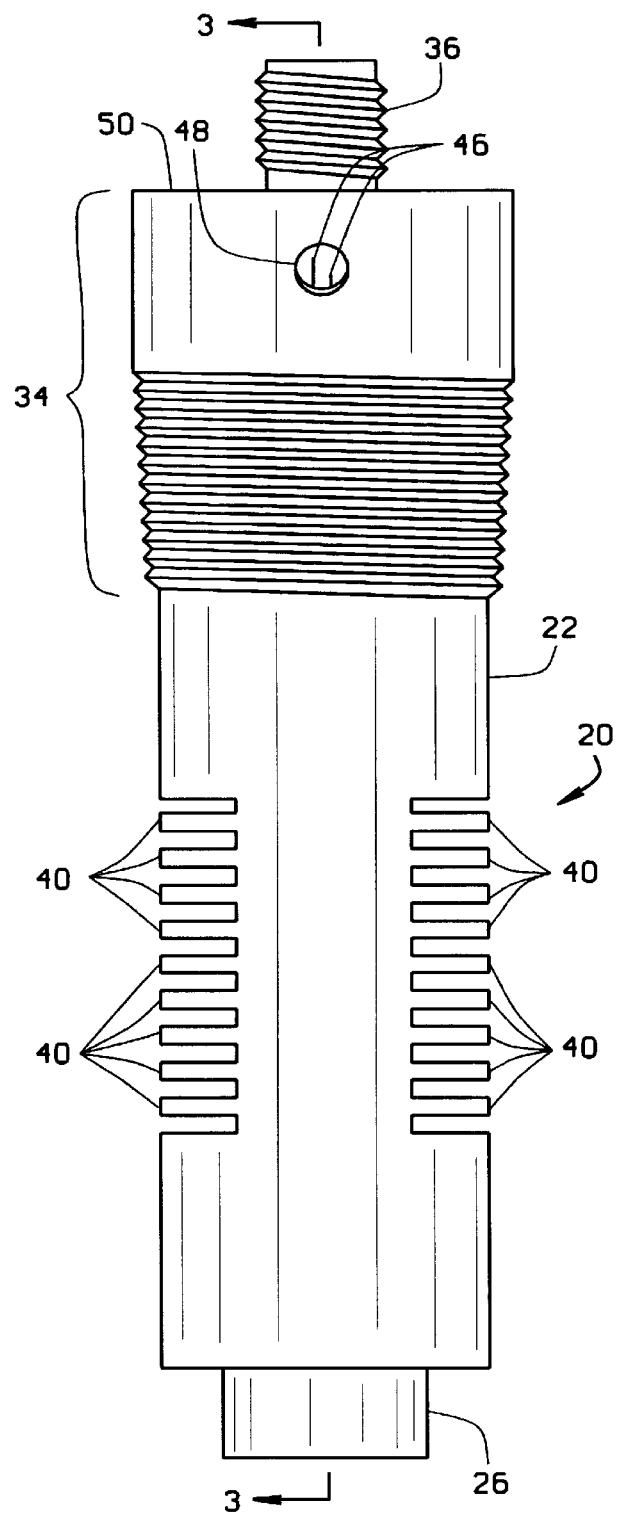
FIG. 1 PRIOR ART
FIG. 2

HEATED INSTRUMENT REGULATOR TIP

FIELD OF THE INVENTION

The present invention relates to tips for instrument regulators, and more particularly to a tip for an instrument regulator which incorporates a heater within.

BACKGROUND OF THE INVENTION

It is often desirable in the natural gas and oil industries to withdraw samples directly from a pipeline for analysis or measurement of various variables. Various instruments are used for this purpose, such as calorimeters, gravitometers, and hydrogen sulfide analyzers. The pipeline can be tapped and a sample drawn directly therefrom, however the pressure of the fluid in a pipeline is often too high for use in the analyzing or measuring instruments. Pipelines carry natural gas at pressures as great as 5000 psig, while many gas analyzing instruments cannot use samples at greater than 100 psig.

U.S. Pat. No. 4,346,611 to Welker ("the '611 patent") demonstrates the use of one type of regulator which is inserted into a pipeline to withdraw a sample and regulate the pressure thereof. The device is inserted into a pipeline so that the tip of the device is near the center of the pipeline, where the samples drawn are the most representative of the pipeline flow.

A regulator is located near the tip of device which reduces the pressure of the sample. In the case of a gas, though, the sudden drop in pressure of the fluid as it flows past the regulator, causes a sudden drop in temperature as well. This effect, known as the Joule-Thomson effect, can cause freezing or liquid carry over into the instrument. Such occurrences can cause damage to the insertion device or the instruments.

To counter the Joule-Thomson effect, regulator tips often have thermal fins attached thereto, thus increasing the surface area of the tip. This allows more thermal energy from the pipeline flow to be absorbed by the tip just beyond the point of regulation. The '611 patent discloses the use of such thermal fins, and most of the regulator tips used in the industry, such as those made by Welker Engineering Company of Sugar Land, Tex., use thermal fins for the same purpose.

Nonetheless, further means are required to counter the Joule-Thomson effect in insertion instrument regulators. It is thus an object of the present invention to provide a regulator tip which will counter the cooling effects of pressure regulation.

It is a further object of the present invention to provide an insertion instrument regulator with a heated tip. Other objects of the invention will become apparent from the specification described herein below.

SUMMARY OF THE INVENTION

In accordance with the objects listed above, a tip for an insertion instrument regulator is provided with means for actively heating the sampled gas beyond the point of regulation.

According to one aspect of the present invention, a prior art regulator tip is adapted to receive a heater. To facilitate the adaptation, the tip is manufactured with a larger diameter than is conventionally used.

The regulator tip is typically made of stainless steel, or similar material, with a substantially cylindrical body. At one end of the body, there is a flange for mounting the tip to the remainder of the regulating device. At the other end thereof, a valve is located at the entrance to an axial bore, thereby defining the point of regulation. Thermal fins are optionally added to the body above the point of regulation for absorbing thermal energy from the gas flow in the pipeline.

In the preferred embodiment, the fins extend only around a portion of the body. A well is provided in the body, such that none of the fins protrude into the well. A heater is then placed inside the well. Power is provided to the heater which limits or prevents cooling of the gas at the point after regulation.

According to another aspect of the present invention, means are provided for supplying power to the heater, wherein the power leads of the heater emerge from the body at some point outside the pipeline.

BRIEF DESCRIPTION OF THE DRAWINGS

So that the manner in which the above-identified features, advantages, and objects of the present invention are attained and can be understood in detail, a more particular description of the invention, briefly summarized above, may be had by reference to the embodiment thereof which is illustrated in the appended drawings.

It is noted, however, that the appended drawings illustrate only a typical embodiment of this invention and is therefore not to be considered limiting of its scope, for the invention may admit to other equally effective embodiments. Reference the appended drawings, wherein:

FIG. 1 is a cross-sectional view of a prior art instrument regulator;

FIG. 2 is a front elevation of the present heated instrument regulator tip;

DETAILED DESCRIPTION OF THE DRAWINGS

Referring now to FIG. 1, a prior art instrument regulator 10 is shown for the purpose of providing a reference point in describing the relationship between an instrument regulator 10 and its tip 12. The present invention is directed toward a new design for the tip.

Figure 3:
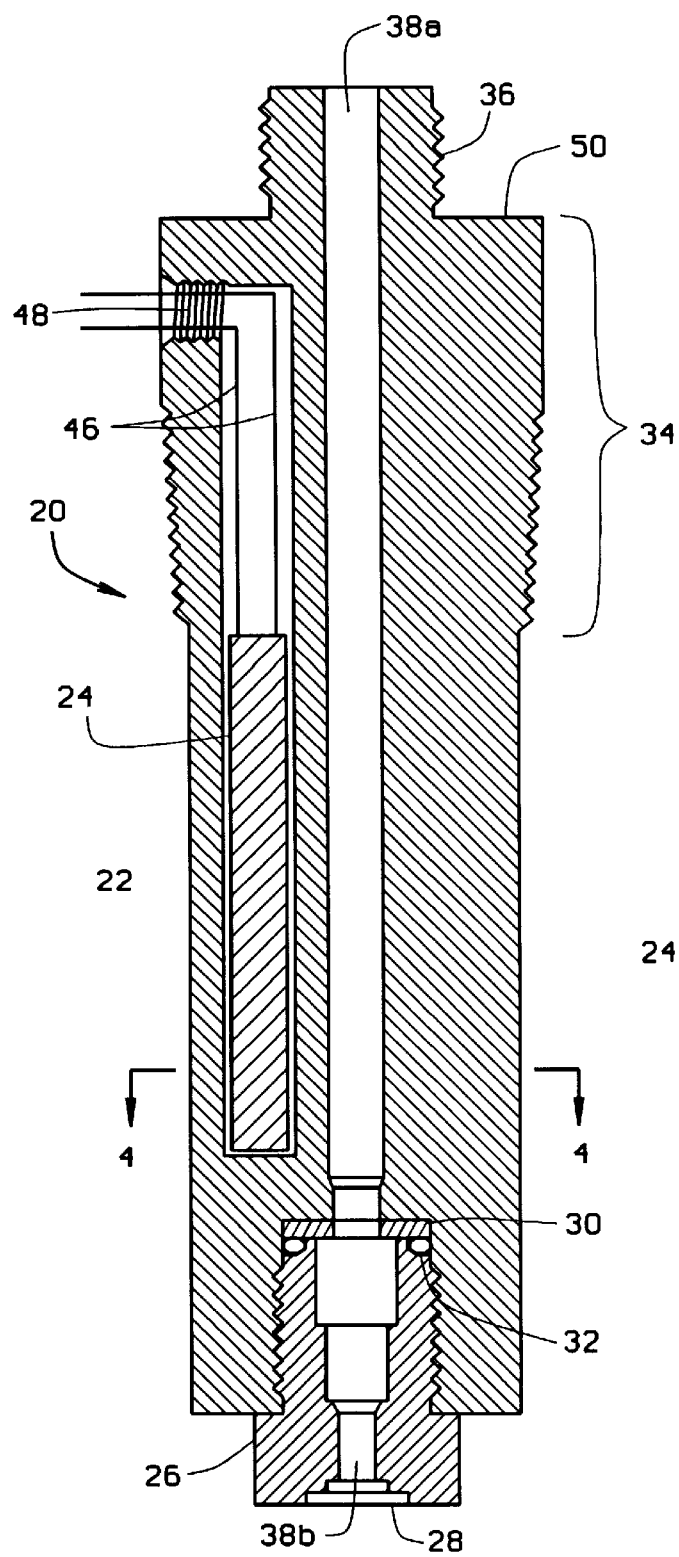
FIG. 3 is a cross-sectional view of the present heated instrument regulator tip taken along line 3—3 of FIG. 2.
Figure 4:
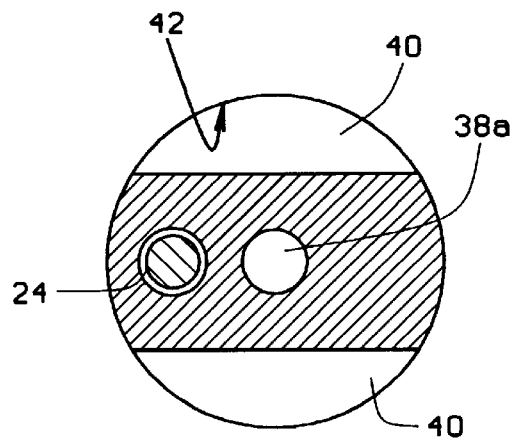
FIG. 4 is a cross-sectional view of the present heated instrument regulator tip taken along line 4—4 of FIG. 3.

The present tip assembly 20 is shown generally in FIG. 2, with cross-sectional views in FIGS. 3 and 4. The tip assembly 20 is composed primarily of a probe 22, a heater 24, and a valve housing 26. The valve housing 26 is unchanged from those used in the prior art. The valve housing is adapted to receive a spring and a valve (not shown) and has an inlet opening 28 to receive a gas sample. When in use, the tip assembly 20 is inserted into a pipeline (not shown), thereby placing the inlet opening 28 in fluid communication with the gas flow of the pipeline.

The probe 22 is adapted to threadedly receive the valve housing 26. A gasket 30 and/or an o-ring 32 may be optionally placed therebetween. In the preferred embodiment, the probe 22 is made of stainless steel, however various materials may be used. It is preferable that the material used for the probe 22 be thermally conductive to increase the efficiency of both the thermal fins 40 and the heater 24. The probe 22 should consist of a generally cylindrical body, though as seen in FIGS. 2 and 3, an upper portion 34 thereof may vary in diameter and have threading 36 for the purposes of coupling to the remainder of the instrument regulator and/or the pipeline.

The probe 22 and the valve housing 26 both have axial bores, respectively 38 a, 38b, throughout their lengths. When coupled, the axial bores 38 a, 38b from each are in fluid communication with each other. The gas sample enters the axial bore 38b of the valve housing 26 through the inlet 28 at one pressure equal to the pressure of the gas inside the pipeline. As the gas flows into the axial bore 38 a of the probe 22 and past the valve, the pressure thereof is decreased according to the setting of the regulator. By way of example, a gas sample from a pipeline with a pressure of 2000 psig may use a regulator that reduces the pressure of the sample to 150 psig.

The rapid reduction in pressure of the gas causes a noticeable decrease in temperature (known as the Joule-Thompson effect). To prevent freezing or the formation of condensation, the gas must be quickly heated back up to the ambient temperature. The present invention uses a heated tip, however it is preferred that it also be used in conjunction with prior art means as well, namely thermal fins 40.

If thermal fins 40 are used, they should not extend beyond the outside diameter of the probe 22, so that the probe 22 may be inserted into and retracted from the pipeline. However, a permanently fixed version of the present invention is contemplated which would not need such a limitation on the length of the thermal fins 40, because the thermal fins 40 would not need to fit any particular clearance for retraction. Unlike the thermal fins used on prior art tips, the present probe 22 must preserve room for the heater 24, therefore it is preferable that the thermal fins 40 do not completely encompass the probe 22. FIG. 4 shows a lateral cross-section taken of the probe 22 between two thermal fins 40, thus showing the preferred configuration thereof. Here the thermal fin 40 was formed by removing a volume of material from the probe 22 defined by the outer surface 42 thereof and a plane parallel to the axis thereof which does not intersect the axial bore 38. The thickness of the volume removed should be approximately equal to the thickness of the thermal fin 40. In the preferred embodiment, each thermal fin 40 on one side has a corresponding identical thermal fin 40 on the opposite side (that is the planes defining the thermal fins should be parallel to one another). The present invention, in some applications, may alleviate the need for thermal fins 40 altogether.

A well 44 is disposed within the probe 22 for receiving a heater 24. The well 44 should be parallel to the axial bore 38 a, but with no overlap such that there is a wall defined therebetween. If thermal fins 40 are used, a section must be left for the placement of the well 44. The bottom of the well 44 should be lubricated to ensure smooth insertion of the heater 24 and efficient heat transfer to the probe 22.

In some prior art tips that used thermal fins, the fins encompassed the entire circumference of the probe. To allow room for the heater well 44 in the present invention, in accordance with the above any thermal fins 40 that may be used should only intrude into the probe body 22 part way. One configuration thereof may be clearly seen in FIG. 4.

The heater 24 has a plurality of leads 46 to provide power thereto. The heater 24 may be a standard cartridge heater, in which the leads 46 connect internally to a resistance wire that generates heat when an electrical current is applied thereto.

When the tip assembly 20 is attached to the instrument regulator, its top surface 50 is inaccessible. Therefore, a small bore 48 (optionally threaded) should be placed toward the top of the probe 22 to allow the leads 46 to exit the tip assembly 20. An external power supply is then connected to the leads 46.

In operation, as gas enters through and past the valve housing 26 via the inlet 28 and bore 38b, the rapid pressure drop causes Joule-Thompson cooling. Before the gas sample can freeze or condense, the thermal fins (if used) absorb thermal energy from the pipeline and transfer it to the cooling gas sample in the bore 38. Primary protection from freezing or condensing gas in the probe 22 is supplied by heater 24, which receives a current from an external power supply. The heater 24 also transfers thermal energy to the gas sample, but at a higher rate than the thermal fins alone.

While the foregoing is directed to the preferred embodiment of the present invention, other and further embodiments of the invention may be devised without departing from the basic scope thereof, and the scope thereof is determined by the claims which follow.

What is claimed is:

1. A pressure regulator tip for insertion into a pressurized gas pipeline to allow a portion of the fluid in the pipeline to be diverted through the regulator at reduced pressure, comprising:

a body having an upper portion having an outlet port and a fastener adapted to attach the valve to the pipeline and a lower portion adapted to be disposed within the pipeline when the fastener is attached to the pipeline and the pipeline is pressurized;

an axial bore within the body and extending through an entire length of said body and in fluid communication with both said inlet port and outlet port;

a regulator valve disposed within said axial bore downstream of the inlet port and within the lower portion, said regulator valve adapted to reduce the pressure of gas flowing from the pipeline through the inlet to the outlet; and a heater disposed within the lower portion of the body in heat transfer adjacency to, but spaced from said axial bore at a point upstream of said outlet port and extending to a point adjacent to at least a downstream side of the regulator valve, said heater located so as not to block the flow of gas through said axial bore.

2. The tip of claim 1, further comprising:

a second bore located within the lower portion and spaced from the axial bore, said heater being disposed in said second bore and said second bore being closed at its lower end.

3. The tip of claim 2, further comprising:

a plurality of power leads attached to the heater extending from outside the regulator to the heater, the heater being completely within the lower portion.

4. The tip of claim 1, further comprising;

a groove in an external surface of the lower portion, said groove increasing the external surface area of the lower portion adjacent the axial bore immediately upstream of the regulator valve to increase the heat transfer from the pipeline to the diverted gas immediately downstream of the regulator valve.

5. The tip of claim 4, further comprising a plurality of grooves in said lower portion, said grooves forming one or more heat transfer fins in an external surface of said lower portion.

6. The tip of claim 1, wherein said heater and axial bore are parallel.

7. A tip for insertion into a pressurized gas pipeline, comprising a body having a fastener adapted to attach the tip to the pipeline with the tip protecting laterally into the pipeline;

a heater well in said body;

an axial bore extending through the entire length of said body with inlet and outlet openings on opposing ends and positioned in heat transfer adjacency to, but spaced from said well, the bore adapted to receive a regulator valve; and a heater element disposed within said well, the element being capable of generating sufficient heat to maintain the axial bore above a desired temperature, whereby gas can be diverted from the pipeline through the tip and the pressure of the diverted gas reduced significantly without excessive condensation in the axial bore.

8. The tip of claim 7, wherein said axial bore has a pressure regulator valve disposed therein between said inlet and said outlet.

9. The tip of claim 7 wherein the outer surface of said tip has a region of increased surface area, thereby varying the heat transfer function of the tip.

10. The tip of claim 7 wherein said heater is a wound resistance wire about a core.

11. The tip of claim 7, wherein said well and axial bore are parallel.

* * * * *